United States Patent [19]

Sheridan et al.

[11] Patent Number: 4,593,690
[45] Date of Patent: Jun. 10, 1986

[54] ENDOTRACHEAL TUBES WITH IMPROVED PROXIMAL END CONNECTOR UNITS

[75] Inventors: David S. Sheridan, Hook Rd., Argyle, N.Y. 12809; Isaac S. Jackson, Greenwich, N.Y.

[73] Assignee: David S. Sheridan, Argyle, N.Y.

[21] Appl. No.: 625,822

[22] Filed: Jun. 28, 1984

[51] Int. Cl.$^4$ ............................................. A61M 16/00
[52] U.S. Cl. ......................... 128/207.15; 128/204.18; 128/912; 138/119; 138/121; 138/173; 138/DIG. 8; 285/122; 285/223; 604/281; 604/283
[58] Field of Search ............... 128/207.14, 207.15, 128/207.16, 207.18, 200.26, 201.11, 912; 604/280, 281, 282, 283, 284, 164; 138/119, 120, 121, 122, 172, 173, 178, DIG. 5, DIG. 8, DIG. 11; 4/207; 285/DIG. 19, 224, 122, 226, 223, 227

[56] References Cited

U.S. PATENT DOCUMENTS

| | | | |
|---|---|---|---|
| 3,388,705 | 6/1968 | Grosshandler | 128/207.14 |
| 3,599,642 | 8/1971 | Tindel | 128/207.14 |
| 3,860,978 | 1/1975 | Wirth | 4/207 |
| 3,873,137 | 3/1975 | Yamaguchi | 285/226 |
| 3,908,704 | 9/1975 | Clement et al. | 138/21 |
| 3,929,165 | 12/1975 | Diebolt et al. | 138/121 |
| 4,050,466 | 9/1977 | Koerbacher | 128/207.14 |
| 4,275,724 | 6/1981 | Behrstock | 604/164 |
| 4,363,323 | 12/1982 | Geiss | 128/207.18 |
| 4,416,273 | 11/1983 | Grimes et al. | 128/207.16 |

OTHER PUBLICATIONS

Ohio Chemical Products Catalog, "Anesthesia Apparatus and Accessories-Endotracheal Tube Adapters", p. 44, 7/20/66.
Ohio Chemical Products Catalog, "Anesthesia Apparatus and Accessories-Jackson Silver Trecheotomy Tube", p. 45, 7/20/66.

Primary Examiner—Henry J. Recla
Attorney, Agent, or Firm—Carroll F. Palmer

[57] ABSTRACT

Conventional endotracheal tubes are provided with improved proximal end connector units by which the endo tubes may be attached to breathing equipment or like fluid flow devices in a manner that mitigates interference with operations being performed on patients intubated with the endo tubes, such units comprising a straight, rigid, cylindrical distal end portion, a straight, rigid, cylindrical proximal end portion, a central tubular portion joining the distal end portion to the proximal end portion, the central tubular portion being bendable in an arc of at least 180° without any substantial diminution of its effective lumen, such proximal end portion, distal end portion and central tubular portion all being integral and formed of the same thin, plastic material, the central tubular portion comprising a plurality of circumferential, angular segments each consisting of a pair of sides that are of unequal length, the central tubular portion being compressed lengthwise by having the shorter side in each segment folded back under its longer side.

7 Claims, 12 Drawing Figures

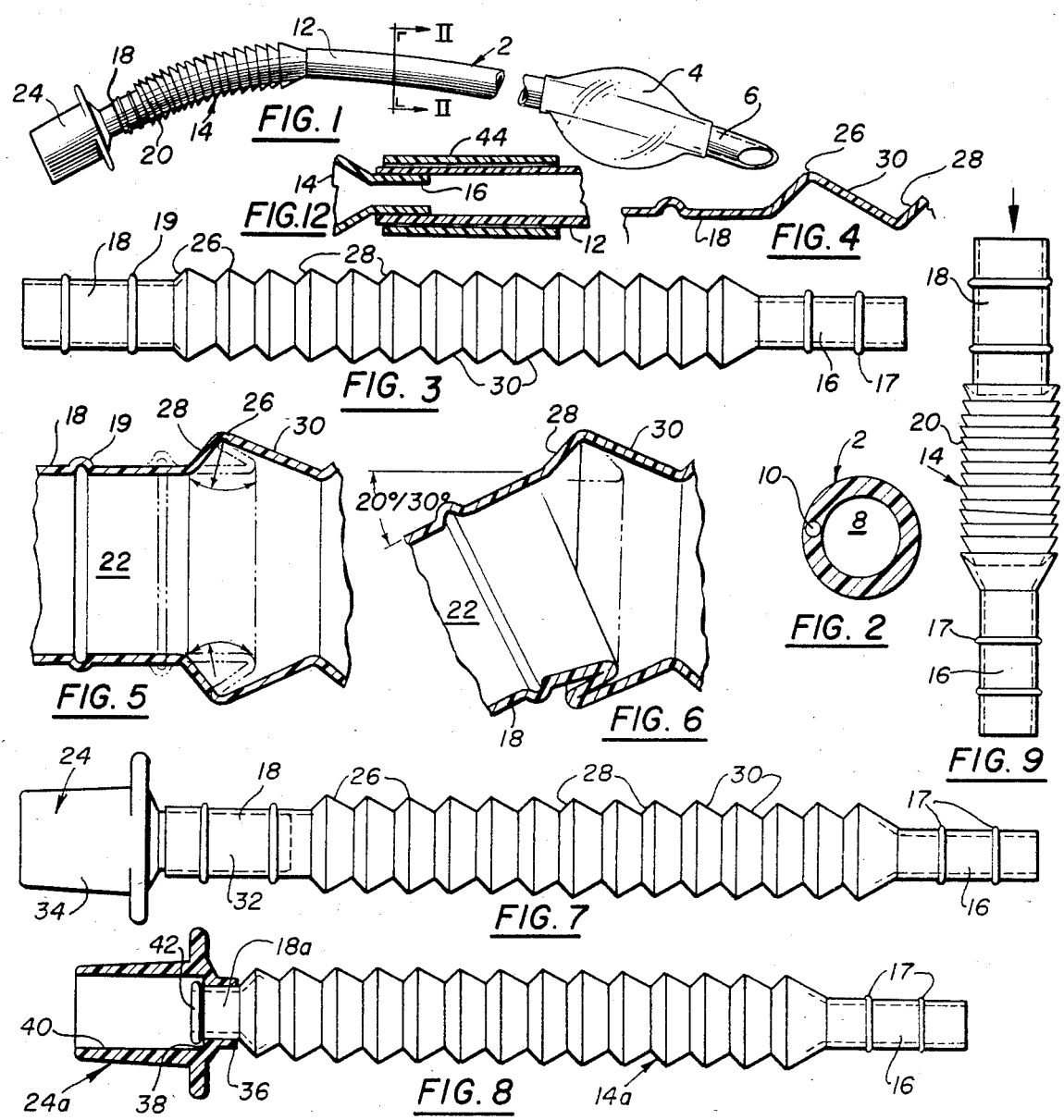
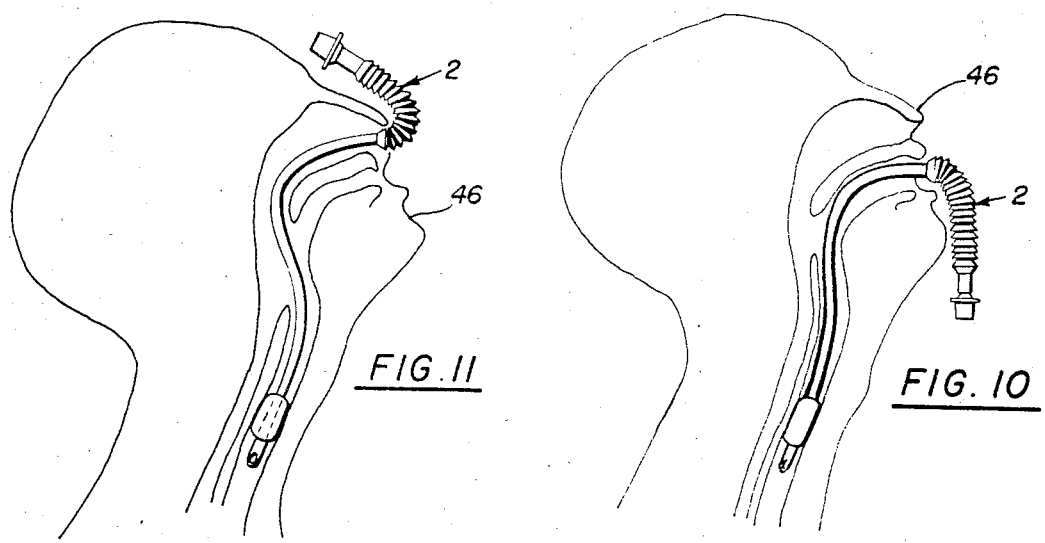

ENDOTRACHEAL TUBES WITH IMPROVED PROXIMAL END CONNECTOR UNITS

BACKGROUND OF THE INVENTION

1. Field of the Invention

This invention relates broadly to endotracheal tubes. More particularly, it concerns endotracheal tubes that have improved connector units fitted to their proximal ends by which the endo tubes may be attached to a breathing circuit or like fluid flow machines in a manner that mitigates interference with operations being performed on patients intubated with the endo tubes.

2. Description of the Prior Art

Conventional endotracheal tubes are arcuate in shape (bowed) intubation of patients, for example, see U.S. Pat. Nos. 3,599,642 and 3,848,605. When such tubes have been properly positioned in the trachea, they assume the anatomical shape.

An intubation can be done via the oral or the nasal route with the choice of route being often determined by the procedure applied to the patient. Hence, endotracheal tube are manufactured with extra length so that anatomical differences between patients will be accommodated and also so the tubes can be used nasally or orally since the nasal route requires a longer tube than the oral route. Quite often, the anesthetist will size the tube to the patient by cutting off approximately 30% at the proximal end . . . Thus, in oral intubations, the extra length of the tracheal tube will extend beyond the mouth. Such excess length can be a concern because there is a possibility that the tube could be accidently bent over and kinked thereby creating a blockage.

Conventionally the endotracheal tubes have a 15.0 mm coupler which adapts them to the breathing circuit which, in turn, connects to a ventilator. The breathing circuit usually consists of two thin wall, corrugated, flexible tubes, usually about 1.25" in diameter. Both are brought to the tracheal tube and joined to it through the 15.0 mm coupler. The position of this rather bulky breathing circuit can create complications for the surgeon operating on the intubated patient.

Some pre-shaped tubes have been manufactured for nasal and oral use. Such tubes for oral use have a bend at the point where the tube exits from the patient's mouth to make the tube extend down across the patient's chin.

Alternatively, such tubes for nasal use have a bend where the tube exits from the patient's nose to take the tube back over the forehead of the patient (see U.S. Pat. No. 3,964,488). However, tubes of these types have the disadvantage of being limited to the two stated directions and the permanent bends in the tubes limit the anesthetists' ability to position the distal end in the trachea. Thus, if the distance from the bend to the distal end tip is too long, as might be the case with a short necked patient, the anesthetist can pull the tube back, but this extends the bend away from the patient. This means that the bend is in the wrong place for that particular patient. It is possible that the opposite can happen with long-necked patients leaving the balloon cuff of the tracheal tube crowding the patient's vocal cords. Another disadvantage is that hospitals using such preformed tubes must stock both the oral and nasal type along with the more widely used bowed tubes.

Other ways of getting the proximal end of tracheal tubes and connection elements out of the way of a surgeon have been developed. For example, one approach is to provide a metal coupler shaped to bend down over the chin of a patient when attached to the proximal end of a conventional tracheal tube (see U.S. Pat. No. 2,912,982). Also, central portions of tracheal tubes have been provided with corrugations to create sections therein that can be bent without kinking the tubes thus enabling the tubes to be shaped to bend in a desired direction (see U.S. Pat. Nos. 4,050,466 and 4,275,724). Yet another approach has been to provide adapters having a flexible, bellows like portion to be attached to the proximal end of tracheal tubes to provide a bendable connection betw the tracheal tubes and anesthesia machines (see U.S. Pat. No. 3,388,705).

The present invention provide a further solution to the problems experienced in the use of endotracheal tubes as discussed above that permits hospitals to stock only the commonly used type of bowed tracheal tubes. At the same time, the anesthetist can size the tube since the invention provides improved type tracheal tubes in which proximal end portions may be cut away to size the tube. Also with these improved tubes, compound bends and directions are easily accomplished. In addition, the new tubes lock into the set shape so that there is no side thrust as can be caused by a resilient bellows type connector such as disclosed in U.S. Pat. No. 3,388,705. Hence, the patients, the anesthetists, the surgeon and the hospitals all benefit from the unique improvements provided by the invention.

OBJECTS

A principal object of the invention is the provision of new, improved forms of endotracheal tubes. Further objects include the provision of:

1. Endotracheal tubes having improved proximal end connector units.

2. Such tubes that may have proximal end portions cut off to size the tubes to patients without impairing the functioning of the tubes.

3. Proximal end connector units for endotracheal tubes that permit the tubes to be connected to breathing circuits in a manner that mitigates interference with operations being performed on patients intubated with the tubes fitted with such connector units.

4. Endotracheal tubes that permit compound bends in the proximal end portions to be easily accomplished.

5. Such tubes that can be intubated both nasally and orally so that hospitals need stock only one type tube for both types of intubations of patients.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished in accordance with the present invention by the provision of permanently bowed endotracheal tubes having an inflatable balloon cuff on their distal end, a central major lumen, a secondary minor lumen via which the cuff can be inflated and a proximal end through which the major lumen exits fitted with an improved proximal end connector unit for connection of the tube to external fluid flow equipment.

Such connector units comprise a straight, rigid, cylindrical distal end portion having an O.D. equal to the diameter of the major lumen of the tracheal tube, a straight, rigid, cylindrical proximal end portion having an I.D. different from the I.D. of the distal end portion, and a central tubular portion joining the distal end portion to the proximal end portion, the central tubular portion being bendable in an arc of at least 180° without any diminution of its effective lumen which is at least equal to the lumen of the tube. The proximal end portion, distal end portion and central tubular portion are all integral and formed of the same thin, plastic material. The central tubular portion comprises a plurality of circumferential, angular segments each consisting of a pair of sides that are of unequal length, the central tubular portion being compressed lengthwise with the shorter side of each of the pair being folded back under the longer side.

In a preferred embodiment, the new endotracheal tubes have a 15.0 mm coupler member inserted in the proximal end portion of the connector unit, the coupler member comprising a tapered, male distal end portion that is inserted into the connector unit and a 15.0 mm male proximal end portion.

In a further embodiment, the cylindrical distal end portion of the connector unit has a plurality of spaced apart, annular, integral beads molded therein. Also, the cylindrical proximal end portion has at least one annular, integral bead molded therein. These bead portions provide stiffness and radial strength to the distal and proximal end portions.

In yet another embodiment, a coupler member is connected to the proximal end portion of the connector unit, which coupler member comprises a male or female proximal end portion and a female distal end portion that surrounds the cylindrical proximal end portion of the connector unit and has a shoulder in its inner surface into which nests there is snapped an annular ring formed on the end of the cylindrical proximal end portion.

Also in preferred embodiments, the shorter side of each of the pair of sides of each angular segment in the connector unit is the proximal side of said segments.

BRIEF DESCRIPTION OF THE DRAWINGS

A more complete understanding of the present invention may be obtained by reference to the accompanying drawings in which:

FIG. 1 is a lateral view of an endotracheal tube made in accordance with the invention.

FIG. 2 is as sectional view taken on the line II—II of FIG. 1.

FIG. 3 is a lateral view of a endotracheal tube connector unit made in accordance with the invention as it is removed from the forming mold.

FIG. 4 is a enlarged, fragmentary, sectional view of a proximal end portion of the connector unit of FIG. 3.

FIG. 5 is another enlarged, fragmentary, sectional view of a proximal end portion of the connector unit of FIG. 3.

FIG. 6 is a view of the proximal end portion of FIG. 5 in a flexed or bent condition.

FIG. 7 is a view similar to FIG. 3 but with a coupler member fitted into the proximal end of the connector unit of FIG. 3.

FIG. 8 is a view similar to FIG. 3 but with another type of coupler member fitted onto the proximal end of the connector unit of the invention.

FIG. 9 is a lateral view of a connector unit like that shown in FIG. 3, but with such unit in a longitudinally compressed condition.

FIG. 10 is a schematic view of an endotracheal tube of the invention used in a typical oral intubation of a patient.

FIG. 11 is a schematic view of an endotracheal tube of the invention used in a typical nasal intubation of a patient.

FIG. 12 is an enlarged, fragmentary, sectional view of another embodiment of endotracheal tubes of the invention comprising a bite block.

DESCRIPTION OF THE PREFERRED EMBODIMENTS

With reference to the accompanying drawings in which identical items are identically numbered, the permanently bowed endotracheal tube 2 comprises an inflatable balloon cuff 4 on its distal end 6, a central major lumen 8, a secondary minor lumen 10 via which the cuff 4 can be inflated, a proximal end 12 through which the major lumen exits, and an improved proximal end connector unit 14 for connection of the tube 2 to external fluid flow equipment (not shown).

The connector unit 14 comprises a straight, rigid, cylindrical distal end portion 16 having an O.D. at least equal to the diameter of the major lumen 8, a straight, rigid, cylindrical proximal end portion 18 having an I.D. different from I.D. of the distal end portion 16, and a central tubular portion 20 joining the distal end portion 16 to the proximal end portion 18.

The central tubular portion 20 is bendable in an arc of at least 180° without diminution of its effective lumen which is at least equal to the lumen of the proximal end portion 18. The proximal end portion 18, distal end portion 16 and central tubular portion 20 are all integral and formed of the same thin, plastic material. The preferred plastic material is polypropylene with about a 75 shore D hardness, but other materials such as polyethylene, ABS, PVC, etc. may be used.

The proximal end portion has a lumen 22 sized to forceably accept a standard 15.0 mm coupler member 24.

The central tubular portion 20 of the unit 14 comprises a plurality of circumferential, angular segments 26 each of which consists of a short side 28 and a long side 30. FIG. 3 shows the unit 14 as it comes from the mold with each of the segments 26 extended. However, for use in the tube 2, the central tubular portion 20 of unit 14 is compressed lengthwise with the shorter side 28 of each segment 26 being folded back under the longer side 30. FIG. 5 shows by dotted lines and dimensional arrows the locking mode when compression takes place in the longitudinal direction. Each segment is deformed slightly as the short sides 28 are forced under the long sides 30 and as the short sides 28 pass center, each is firmly held. The compressed unit 14, as seen in FIG. 9, will stay locked in this compressed condition until it is forceably bent. At bending, the outside radius opens while the inside radius stays locked (see FIG. 6). This feature maintains the locked condition in the bent form. One segment bent as shown in FIG. 6 results in 20° to 30° of bend. FIG. 6 is a sectional view of one side of a segment 26 and shows the geometric arrangement of the locking feature.

Annular beads may be used to add stiffness and radial strength to to the proximal and distal end portions 18 & 16 of the unit 14. Thus, the cylindrical distal end portion 16 has a plurality of spaced apart, semicircular, integral, annular beads 17 molded therein. Additionally, the cylindrical proximal end portion 18 has at least one semicircular, integral, annular bead 19 molded therein. The beads 17, in addition to adding stiffness and radial strength to the end portion 16, assist in holding the unit 14 locked into the proximal end 12 of the endotracheal tube 2. Alternatively, the portions 16 and 19 can be angular barbs (not shown).

The endotracheal tube 2 of the invention has a standard 15.0 mm coupler member 24 inserted in the proximal end portion 18 of the connector unit 14. Such coupler member 24 comprises a tapered, male distal end portion 32 that is inserted into said connector unit and an enlarged, male proximal end portion 34 (see FIGS. 1 & 7). In this assembly, the coupler member 24 is joined to the unit 14 by a press fit preventing any relative movement between the parts.

The endotracheal tubes 2 of the invention may have another design of 15.0 mm coupler member 24a connected to the proximal end portion 18a of the connector unit 14a. Such coupler member 24a comprises a female proximal end portion 34 and a female distal end portion 36 that surrounds the cylindrical proximal end portion 18a of the connector unit 14a and has a shoulder 38 in its inner surface 40 behind which an annular ring 42 on the cylindrical proximal end portion 18a snaps to lock the member 24a to the unit 14a. Clearance between the coupler member 24a and unit 14a permits the 15.0 mm coupler member to swivel freely. Medical grade grease is applied in the assembly of the parts to lubricate the parts connection and help to seal against gas leaks. The annular ring 42 is of barbed shape with its flat, distal side locking against a mating flat side of the shoulder 38 for safe retention of the coupler member 24a in the unit 14a. The swivel arrangement as described relieves torque that may be introduced to the assembly by the breathing circuits (not shown).

In the embodiment of the invention shown in FIG. 12, a small length of rigid plastic tubing 44 is slipped over the proximal end 12 of the endo tube 2 before connecting the unit 14 to the tube 2 and then sliding the tubing 44 back over the junction the the unit 14 meets the proximal end 12. The tubing 44 acts as a bite block when the endo tube 2 is intubated orally.

FIGS. 10 and 11 illustrate oral and nasal intubation respectively with the improved endotracheal tubes of the invention. They illustrate that in either case, the connector units 14 or 14a can be directed in any direction above the patient's face 46.

The embodiments of the invention in which an exclusive property or privilege is claimed are defined as follows:

1. In a permanently bowed endotracheal tube having an inflatable balloon cuff on its distal end, a central major lumen, a secondary minor lumen via which the cuff can be inflated and a proximal end through which the major lumen exits, an improved proximal end connector unit for connection of said tube to external fluid flow equipment which comprises:

a straight, rigid, cylindrical distal end portion having an O.D. approximately equal to said lumen of said tube, a straight, rigid, cylindrical proximal end portion having an I.D. larger than said I.D. of said distal end portion, and a central tubular portion joining said distal end portion to said proximal end portion, said central tubular portion being bendable in an arc of at least 180° without any substantial diminution of its effective lumen which is at least equal to the lumen of said tube, said proximal end portion, distal end portion and central tubular portion all being integral and formed of the same thin, plastic material, said central tubular portion comprising a plurality of circumferential, angular segments each consisting of a pair of sides that are of unequal length, said central tubular portion being compressed lengthwise with the shorter side of each of said pair being folded back under the longer side, said connector unit being attached to said endotracheal tube by insertion of said distal end portion in said proximal end of said endotracheal tube.

2. The endotracheal tube of claim 1 having a coupler member inserted in said proximal end portion of the connector unit, said coupler member comprising a tapered, male distal end portion that is inserted into said connector unit and an enlarged, male proximal end portion.

3. The endotracheal tube of claim 1 wherein said cylindrical distal end portion has a plurality of spaced apart, annular, integral beads molded therein.

4. The endotracheal tube of claim 1 wherein said cylindrical proximal end portion has at least one annular, integral bead molded therein.

5. The endotracheal tube of claim 1 having a coupler member connected to said proximal end portion of said connector unit, said coupler member comprising a female distal end portion that surrounds said cylindrical proximal end portion and having a shoulder in its inner surface, an annular ring on the end of said cylindrical proximal end portion, said annular ring bearing against said shoulder to retain said coupler member on said connector unit.

6. The tube of claim 5 wherein said coupler member shoulder and said annular ring are sized so that said coupler member may swivel freely on said connector unit without gas leakage through the junction between said shoulder and said annular ring.

7. The endotracheal tube of claim 1 wherein the shorter side of each of said pair of sides is the proximal side of said segments.

* * * * *